United States Patent [19]

Engbert et al.

[11] Patent Number: 4,692,550

[45] Date of Patent: Sep. 8, 1987

[54] CONTINUOUS PROCESS FOR THERMAL SPLITTING OF CARBAMIC ACID ESTERS

[75] Inventors: Theodor Engbert; Günter Hammen, both of Dormagen; Hartmut Knöfel, Odenthal; Klaus König, Leverkusen, all of Fed. Rep. of Germany

[73] Assignee: Bayer Aktiengesellschaft, Bayerwerk, Fed. Rep. of Germany

[21] Appl. No.: 485,347

[22] Filed: Apr. 15, 1983

[30] Foreign Application Priority Data

Apr. 27, 1982 [DE] Fed. Rep. of Germany ....... 3215591

[51] Int. Cl.$^4$ ............................................ C07C 118/00
[52] U.S. Cl. .................................................. 560/345
[58] Field of Search ...................... 260/453 P; 560/345

[56] References Cited

U.S. PATENT DOCUMENTS

| | | | |
|---|---|---|---|
| 2,409,712 | 10/1946 | Schweitzer | 260/453 P |
| 2,692,275 | 10/1954 | Bortnick | 260/453 P |
| 2,713,591 | 7/1955 | Bortnick | 260/453 P |
| 2,727,020 | 12/1955 | Melamed et al. | 260/80.3 |
| 3,734,941 | 5/1973 | Sydor | 260/453 P |
| 3,870,739 | 3/1975 | DeLaMater et al. | 260/453 P |
| 3,919,278 | 11/1975 | Rosenthal et al. | 260/453 P |
| 3,919,279 | 11/1975 | Rosenthal et al. | 260/453 P |
| 3,919,280 | 11/1975 | Rosenthal et al. | 260/453 P |
| 3,962,302 | 6/1976 | Rosenthal et al. | 260/453 P |
| 4,081,472 | 3/1978 | Tsumura et al. | 260/453 P |
| 4,294,774 | 10/1981 | Henson et al. | 260/453 P |
| 4,386,033 | 5/1983 | König et al. | 260/453 P |

FOREIGN PATENT DOCUMENTS

| | | |
|---|---|---|
| 54-39002 | 3/1979 | Japan . |
| 54-88201 | 7/1979 | Japan . |
| 54-88222 | 7/1979 | Japan . |

OTHER PUBLICATIONS

A. W. Hoffmann, Berichte der Deutschen Chemischen Gesellschaft, vol. 3, pp. 653 et seq. (1870).
M. Metayer, Bull. Soc. Chim. France, (1951), pp. 802 et seq.
H. Schiff, Berichte der Deutschen Chemischen Gesellschaft, vol. 3, pp. 649 et seq. (1870).
E. Dyer & G. C. Wright, J. Amer. Chem. Soc., vol. 81, (1959), pp. 2138 et seq.
Abbate et al., Journal of Applied Polymer Science, vol. 16, 1972, p. 1213.

*Primary Examiner*—Alan Siegel
*Attorney, Agent, or Firm*—Gene Harsh; Joseph C. Gil; Lyndanne M. Whalen

[57] ABSTRACT

N-monosubstituted carbamic acid esters are thermally split on a continuous basis in a tube reactor. The carbamic acid ester which is flowed down or passed over the inner wall of a tube reactor is thermally split at a temperature of from 150° to 450° C. and under a pressure of from 0.001 to 20 bar into at least two fractions. One fraction is predominantly isocyanate and a second fraction is predominantly hydroxyl compound. These fractions may be separated by removing one as a gaseous fraction formed under the splitting conditions from the head of the reactor and collecting the second fraction as a liquid which accumulates at the base of the reactor. If both fractions are gaseous under the splitting conditions, they are both removed from the head of the reactor and subsequently separated by fractionating columns for example. This process is particularly advantageous in that isocyanate and hydroxyl fractions are obtained in high yield without using a solvent.

10 Claims, No Drawings

CONTINUOUS PROCESS FOR THERMAL SPLITTING OF CARBAMIC ACID ESTERS

BACKGROUND OF THE INVENTION

This invention relates to a continuous process for thermal splitting of carbamic acid esters.

The thermal splitting of carbamic acid esters has been known for some time. The work of A. W. Hoffmann (Berichte der Deutschen Chemischen Gesellschaft, Vol. 1870, pages 653 et seq) and M. Metayer (Bull. Soc. Chim. France, Vol. 1951, pages 802 et seq), has shown that such thermal splitting is reversible, i.e. when the hot reaction mixtures are cooled, the isocyanatee recombine with alcohols and carbamic acid esters are reformed. Special measures must therefore be taken to ensure that the isocyanates and alcohols formed in the thermal splitting of carbamic acid esters can be separately obtained.

U.S. Pat. No. 2,409,712 describes a process by which monofunctional isocyanates may be obtained in batches in moderate yields by heating the corresponding carbamic acid esters in batches to temperatures of from 150° to 450° C. The cleavage products may then be separated by rapid distillation or by introduction into a solvent system which selectively dissolves the isocyanate and the alcohol (for example a mixture of cyclohexane and water). Although this disclosed process is well suited for batch production of monofunctional isocyanates on a laboratory scale, it is commercially impractical due to the fact that it can be carried out only in batches and only moderate yields are obtained. This disclosure does not, however, teach anything with respect to suppression of the formation of secondary products which form during the thermal splitting of carbamic acid esters. Nor does this disclosure teach how to eliminate or at least reduce the adverse effects which such secondary products have on the commercial operation of the splitting process.

Studies conducted by H. Schiff (Berichte der Deutschen Chemischen Gesellschaft, Vol. 1870, pages 649 et seq) and by E. Dyer and G. C. Wright (J. Amer. Chem. Soc., Vol. 81, 1959, pages 2138 et seq) show that, under thermal load, carbamic acid esters can undergo complete or partial, irreversible decomposition to form different products. These possible products include substituted ureas, biurets, carbodiimides, isocyanurates, secondary amines, olefins and/or carbon dioxide.

Various processes have been developed with a view to suppressing the formation of undesirable secondary products in the thermal splitting of carbamic acid esters. One obvious possibility is to minimize the thermal load imposed during the splitting process. If this alternative is used, the thermal splitting process generally must be carried out in the presence of a catalyst because otherwise the volume/time yields would be too low to be practical.

U.S. Pats. Nos. 2,713,591; 2,692,275; 2,727,020 and 4,294,774 and Japanese Patent Application No. 54-88201 (1979) describe processes for the production of isocyanates by thermal splitting of carbamic acid esters in the presence of basic catalysts. However, such basic catalysts lead to increased, irreversible decomposition reactions of carbamic acid esters and isocyanates (cf. for example J. Appl. Polym. Sci., Vol. 16, 1972, page 1213). Accordingly, processes using basic catalysts only give acceptable yields of isocyanate when the carbamic acid esters used are protected against decomposition by appropriate substituents.

Another possible method for suppressing secondary reactions in the thermal splitting of carbamic acid esters is to dilute the carbamic acid esters and/or the cleavage products with inert diluents. U.S. Pat. No. 3,919,279, German Offenlegungsschrift No. 2,635,490 and Japanese Patent Application Nos. 54-39002 (1979) and 54-88222 (1979) describe processes in which the thermal splitting of carbamic acid esters is carried out in inert solvents, optionally in the presence of certain catalysts. In addition to inert solvents, carrier gases, optionally in the form of evaporated low-boiling solvents, are used in the processes described in German Auslegeschriften Nos. 2,421,503 and 2,526,193. However, the use of solvents in the thermal splitting of carbamic acid esters gives rise to considerable difficulties. The solvent used must be stable and inert to isocyanates under the thermolysis conditions. The solvent must also be readily miscible with the carbamic acid esters to be split and its vapor pressure at the temperatures applied must be low enough that it will remain substantially in the liquid phase during the thermolysis process. The choice of possible solvents is seriously limited by these requirements. Suitable, inexpensive solvents are particularly difficult to find in cases where the carbamic acid esters to be split have high molecular weights. In addition, the use of solvents reduces the volume/time yields of isocyanates. Further, in cases where high-boiling solvents are used, it is difficult to distill off the pure components of the liquid reaction mixtures (residues of isocyanate, carbamic acid ester and solvent) from the residue, as proposed for example in German Auslegeschrift No. 2,530,001. In any event, considerable extra effort is involved in working up and storing inert solvents.

The above-mentioned processes for the thermal splitting of carbamic acid esters depend on the use of diluting solvents particularly where polyfunctional carbamic acid esters are used for splitting. If such solvents were not used, the isocyanato-urethanes inevitably accumulating in the reaction mixture would continue reacting to a considerable extent to form undesirable secondary products.

The thermal splitting of monofunctional carbamic acid esters may, however, be carried out in the absence of diluting solvents without serious losses of yield. This is shown, for example, by the process for the thermal splitting of monofunctional carbamic acid alkyl esters described in an earlier, but unpublished German Patent Application No. P 30 47 898.9 (European Patent Application No. 81 110 204.5). This process is, however, disadvantageous in that relatively long residence times for the carbamic acid alkyl esters to be split are necessary.

Finally, splitting processes in which carbamic acid esters are split at high temperatures (400° to 600° C. or 350° to 550° C.) in the gas phase are described in U.S. Pats. No. 3,734,941 and 3,870,739. In these processes, it is important that the residence time of the gases in the high-temperature zone remain as short as possible because otherwise the carbamic acid esters and/or the cleavage products undergo serious decomposition under the effect of the high thermal load, despite dilution by the gas phase. However, such short residence times can result in yields of isocyanates which are undesirably small. Further, these processes require considerable technical outlay because gases are difficult to heat and cool over short periods of time due to their poor thermal conductivity.

SUMMARY OF THE INVENTION

It is an object of the present invention to provide a process for the continuous thermal splitting of N-monosubstituted carbamic acid esters.

It is also an object of the present invention to provide a process for the continuous thermal splitting of N-monosubstituted carbamic acid esters which is both technically practical and inexpensive.

It is another object of the present invention to provide a process for the continuous thermal splitting of N-monosubstituted carbamic acid esters which produces monoisocyanates and polyisocyanates in high yields.

It is yet another object of the present invention to provide a process for the continuous thermal splitting of N-monosubstituted carbamic acid esters which may be conducted in the absence of a solvent.

These and other objects which will be apparent to those skilled in the art are accomplished by thermally splitting an N-monosubstituted carbamic acid ester under a pressure of from 0.001 to 20 bar and a temperature of from 150° to 450° C. in a tube reactor into at least two fractions. The carbamic acid esters to be split are flowed down or passed over the inner wall of the tube reactor in liquid form. The fractions formed are separated by removing gaseous fractions at the head of the tube reactor and by collecting any liquid fraction which accumulates at the base of the tube reactor. The tube reactor may be a tubular thin-layer or falling-film evaporator.

DETAILED DESCRIPTION OF THE INVENTION

The present invention relates to a process for the continuous thermal splitting of N-monosubstituted carbamic acid esters under a pressure of from 0.001 to 20 bars and at a temperature of from 150° to 450° C. This thermal splitting is followed by separation of the cleavage products into a fraction consisting predominantly of the isocyanate component of the carbamic acid esters (hereinafter referred to as "fraction A") and a fraction consisting predominantly of the hydroxyl component of the carbamic acid esters (hereinafter referred to as "fraction B"). The thermal splitting process is carried out in a tube reactor with the carbamic acid esters to be split running down or being passed over the inner wall of the tube reactor in liquid form. The cleavage products which accumulate in gaseous form under the reaction conditions are removed at the head of the tube reactor. Those cleavage products, if any, which accumulate in liquid form under the reaction conditions are removed at the base of the tube reactor.

Suitable starting materials for the process of the present invention are any N-monosubstituted carbamic acid esters having an isocyanate and/or hydroxyl component with a boiling point below 250° C. under a pressure of 0.01 bar. It is preferred to use carbamic acid esters which have a boiling point that is at least 10° C. above the boiling point of the higher boiling cleavage product under the pressure prevailing in the reactor and which has isocyanate and hydroxyl components with boiling points differing from one another by at least 50° C. under normal pressure. Carbamic acid esters particularly suitable for use in the process of the present invention are those corresponding to the general formulae $$R^1(NHCO_2R^2)_x \text{ or } (R^1NHCO_2)_y R^2$$

in which $R^1$ represents a hydrocarbon radical with a total of from 1 to 18 carbon atoms optionally containing inert substituents and/or being olefinically unsaturated, a cycloaliphatic hydrocarbon radical with a total of 3 to 18 carbon atoms optionally containing inert substituents and/or being olefinically unsaturated, an araliphatic hydrocarbon radical with a total of 7 to 18 carbon atoms optionally containing inert substituents, or an aromatic hydrocarbon radical with a total of 6 to 18 carbon atoms, optionally containing inert substituents (the radical $R^1$ being x-functional or monofunctional radical), $R^2$ represents an aliphatic hydrocarbon radical with a total of 1 to 18 carbon atoms optionally containing inert substituents and/or being olefinically unsaturated, a cycloaliphatic hydrocarbon radical with a total of 4 to 18 carbon atoms optionally containing inert substituents and/or being olefinically unsaturated, an araliphatic hydrocarbon radical with a total of 7 to 18 carbon atoms optionally containing inert substituents, or an aromatic hydrocarbon radical with a total of 6 to 12 carbon atoms optionally containing inert substituents (the radical $R^2$ being a mono-functional or y-functional radical), and x and y (which may be the same or different) represent a number from 1 to 3. The carbamic acid esters corresponding to the above general formulae should preferably have a boiling point that is at least 10° C. above the boiling point of the higher boiling cleavage product under the pressure prevailing in the reactor and have isocyanate and hydroxyl components with boiling points differing from one another by at least 50° C. at normal pressure.

Typical examples of suitable N-monosubstituted carbamic acid esters are N-methyl carbamic acid decyl ester; N-methyl carbamic acid dodecyl ester; N-methyl carbamic acid octadecyl ester; N-methyl carbamic acid eicosanyl ester; N-methyl carbamic acid (2-phenoxyethyl)-ester; N-methyl carbamic acid benzyl ester; N-methyl carbamic acid-(4-chlorobenzyl)-ester; 1,6-bis-(N-methylcarbamoyloxy)-hexane; 1,10-bis-(N-methylcarbamoyloxy)-decane; 1,12-bis-(N-methylcarbamoyloxy)-dodecane; 1,18-bis-(N-methylcarbamoyloxy)-octadecane; 2,2'-bis-(N-methylcarbamoyloxy)-diethyl ether; 1,2-bis-91 2-(N-methylcarbamoyloxy)-ethoxy-ethane; 1,4-bis-(N-methylcarbamoyloxy)-cyclohexane; 4,4'-bis-(N-methylcarbamoyloxy)-2,2-dicyclohexyl-propane); 1,3-bis-91 (N-methylcarbamoyloxy)-methyl-benzene; 1,3,6-tris-(N-methylcarbamoyloxy)-hexane; N-ethylcarbamic acid octyl ester; N-ethyl carbamic acid octadecyl ester; N-ethyl carbamic acid-2-(2-butoxyethoxy)-ethyl ester; N-butyl carbamic acid octadecyl ester; N-methoxy methyl carbamic acid dodecyl ester; N-(2-methoxyethyl)-carbamic acid dodecyl ester; N-hexyl carbamic acid methyl ester; N-octyl carbamic acid ethyl ester; N-(2-methyl-1-hexanyl)-carbamic acid ethyl ester; N-octadecyl carbamic acid butyl ester; N-cyclohexyl carbamic acid octadecyl ester; N-cyclohexyl carbamic acid ethyl ester; N-benzyl carbamic acid ethyl ester; N-allyl carbamic acid-(2-ethylhexyl)-ester; N-(2-phenylethyl)-carbamic acid ethyl ester; N-phenyl carbamic acid methyl ester; N-phenyl carbamic acid propyl ester; N-(4-chlorophenyl)-carbamic acid ethyl ester; N-(3,4-dichlorophenyl)-carbamic acid butyl ester; N-(4-cyclohexyl phenyl)-carbamic acid ethyl ester; N-(3-methylphenyl)-carbamic acid ethyl ester; N-(4-methoxycarbonylphenyl)-carbamic acid ethyl ester; N-1-naphthyl carbamic acid methyl ester; N-phenyl carbamic acid octadecyl ester; N-phenyl carbamic acid dodecyl ester; 1,6-bis-(N-ethylcarbamoyloxy)-hexane; 1,8-bis-(N-propyl-carbamoyloxy)-octane; 1,6-bis-(N-methoxymethyl-carbamoyloxy)-hexane; 1,12-bis-(N-butylcarbamoyloxy)-dodecane; 1,18-bis-(N-2-butoxyethylcarbamoyloxy)-octadecane; 1,12-bis-(N-phenylcarbamoyloxy)-dodecane; 1,12-bis-(N-benzylcarbamoyloxy)-octadecane; 4,4'-bis-(N-butylcarbamoyloxy)-(2,2-dicyclohexylpropane); 1,1,1-tris-[(N-ethylcarbamoyloxy)-methyl]-propane; 1,3,6-tris-(N-phenylcarbamoyloxy)-hexane; 1,2-bis-(cyclohexoxycarbonylamino)-ethane; 1,4-bis-(ethoxycarbonylamino)-butane; 1,6-bis-(ethoxycarbonylamino)-hexane; 1,8-bis-(ethoxycarbonylamino)-octane; 1-(n-butoxycarbonylamino)-3,3,5-trimethyl-5-(n-butoxycarbonylaminomethyl)-cyclohexane; 1,4-bis(ethoxycarbonylamino)-cyclohexane; 4,4'-bis-(ethoxycarbonylamino)-dicyclohexylmethane; 1-methyl-2,4-bis-(ethoxycarbonylamino)-benzene; 1-methyl-2,6-bis(ethoxycarbonylamino)-benzene; 1,5-bis-(butoxycarbonylamino)-naphthalene; 1,3-bis-(ethoxycarbonylaminomethyl)-benzene; 2,4'-bis-(ethoxycarbonylaminio)-diphenylmethane; and 4,4'-bis-(ethoxycarbonylamino)-diphenylmethane.

Mixtures of the 2,4'- and 4,4'-bis-(alkoxycarbonylamino) -diphenylmethanes mentioned above and their corresponding higher-nuclear homologs, in which more than two alkoxycarbonylamino-substituted benzene rings are attached to one another through methylene bridges, are also suitable for the process of the present invention. These "carbamate mixtures of the diphenylmethane series" may be formed in the acid-catalyzed condensation of mono-alkoxycarbonylamino-substituted benzenes with formaldehyde.

Other suitable starting materials include: N-monosubstituted carbamic acid aryl esters such as N-methyl carbamic acid phenyl ester; N-methyl carbamic acid-(3-methylphenyl)-ester; N-ethyl carbamic acid-(2,4-dimethylphenyl)-ester; N-butyl carbamic acid-(nonylphenyl-ester; N-cyclohexyl carbamic acid-(dodecylphenyl-ester; N-octadecyl carbamic acid phenyl ester; 1,4-bis-[(3-isopropyl-5-methylphenoxy)-carbonylamino]-butane; 4,4'-bis-(phenoxycarbonylamino)-diphenylmethane; 4,4'-bis-(phenoxycarbonylamino)-dicyclohexyl methane; 1,8-bis-(phenoxycarbonylamino)-4-(phenoxycarbonylaminomethyl)-octane; 1,3-bis-(N-methylcarbamoyloxy)-benzene; 4,4'-bis-(N-ethylcarbamoyloxy)-biphenyl and 2,2'-bis-(4-N-propylcarbamoyloxyphenyl)-propane. However, these O-aryl carbamic acid esters are less preferred than the carbamic acid esters previously described which have aliphatic, cycloaliphatic or araliphatic radicals on the oxygen atom of the carbamic acid ester group.

Carbamic acid esters containing heterocyclic structural units, such as for example tris-[6-ethoxycarbonylamino)-hexyl]-isocyanurate or tris-[6-phenoxycarbonylamino)-hexyl]-isocyanurate, may also be used as starting materials in the process of the present invention.

The carbamic acid esters useful in the process of the present invention may be obtained by methods known to those in the art. For example, they may be produced by reacting the corresponding amines with chloroformic acid esters or by carbonylating corresponding nitro compounds in the presence of alcohols. They may also be made by condensation of simple carbamic acid esters with formaldehyde or with other aldehydes or even ketones or by reacting amines with urea and alcohols. The method by which the carbamic acid esters are produced does not affect their suitability for the process of the present invention.

Monofunctional and polyfunctional carbamic acid esters may be smoothly split, even in undilute and liquid form, into isocyanates and hydroxyl compounds if the carbamic acid esters are passed in a thin layer over the inner wall of a tube which has been heated to a sufficiently high temperature. In the process of the present invention secondary reactions are suppressed if the residence time of the carbamic acid esters in the hot zone of the splitting reactor is kept very short and the cleavage products (isocyanate and hydroxy compound) are quickly removed from the reaction zone. In addition, it is important during the splitting reaction to maintain a minimum temperature (dependent upon the type of carbamic acid ester to be split and any auxiliaries used), below which complete splitting of the carbamic acid ester is no longer guaranteed.

The removal of the cleavage products from the splitting reactor may be carried out in various ways, as will be explained in more detail hereinafter. In the preferred embodiment of the process of the present invention, the cleavage products (isocyanate and hydroxy compound) accumulate in gaseous form under the reaction conditions. The gaseous product mixture is removed at the head of the reactor and, optionally after the preliminary separation of entrained, unsplit or only partially split starting material, is selectively condensed in two suitably tempered fractionating columns arranged one behind the other, resulting in the accumulation of fraction A (consisting predominantly of isocyanate) and fraction B (consisting predominantly of the hydroxy compound).

In another embodiment of the process of the present invention, the hydroxy compound is removed from the splitting reactor in gaseous form and the isocyanate is removed in liquid form. Alternatively, the hydroxy compound may be removed from the splitting reactor in liquid form and the isocyanate in gaseous form. Although there is no need to separate the gas stream leaving the splitting reactor when either of these embodiments is employed, working up by distillation of the liquid phase removed at the base of the reactor is often advisable, particularly in cases where high boiling liquids or other involatile auxiliaries and additives are used in order to obtain the cleavage products accumulating as liquid in pure form.

The splitting reactors suitable for carrying out the process according to the invention may be designed in many different ways. The only requirement is that the reactor should be operable in a manner such that the carbamic acid ester introduced into the splitting zone is able to distribute in the form of a thin layer over the heated inner wall of the tube and in such a way that the gaseous and/or liquid cleavage products can be removed from the reaction zone in the manner previously described.

In the case of vertically arranged tube reactors, the carbamic acid ester introduced may be distributed over the inner wall of the tube without the assistance of special fittings if the carbamic acid ester to be split is applied uniformly over the wall of the tube by suitable means, for example by a nozzle. However, the carbamic acid ester introduced may also be distributed over the inner wall of the tube with the assistance of a mechanical stirrer or similar means. In cases where the tube reactors are not vertically arranged, the use of a stirrer or other suitable device is generally essential. Stirrers may also be used to transport the material situated on the wall of the tube by inhibiting the downwardly directed flow of the liquid film. In the case of obliquely or horizontally arranged reactors, stirrers may be useful in transporting the carbamic acid ester introduced or the non-gaseous cleavage or decomposition products beyond the splitting zone to the end of the tube.

Examples of suitable splitting reactors are glass, quartz or metal tubes operating as falling-film evaporators, tube reactors equipped with screw-like stirrers and optionally tapering towards their ends and conventional thin-layer evaporators in various forms. Of these splitting reactors, thin-layer evaporators equipped with mechanical stirrers have been found to be particularly advantageous.

In cases where a thin-layer or falling-film evaporator is used for carrying out the process of the present invention, the carbamic acid ester to be split is introduced into the splitting reactor in liquid and, preferably, undiluted form above the actual splitting zone in such a way that the ester runs down the inner wall of the reactor. The inner wall of the reactor is heated to the optimal splitting temperature. The carbamic acid ester is in the form of a thin liquid film either without taking any further measures or after it has been distributed by a stirrer mounted in the reactor.

The splitting temperature has to be selected in such a way that complete splitting of the carbamic acid ester occurs within the average residence time in the splitting zone. For an average residence time of from 0.01 to 10 minutes and preferably from 0.1 to 5 minutes, a temperature in the range from 150° to 450° C. and preferably in the range from 200° to 400° C. has proven to be adequate in most cases.

In some cases, it can also be of advantage to divide the splitting zone into two or more sections each of which is maintained at a different temperature.

The splitting process of the present invention takes place smoothly if the carbamic acid ester introduced is continuously depleted in the film of liquid running down the wall of the reactor and if very little starting material arrives at the end of the splitting zone. The process according to the present invention for the thermal splitting of carbamic acid esters may of course also be carried out in such a way that the carbamic acid ester is not completely split. In this latter case, a product which contains the unchanged starting material and/or the starting material partly split into isocyanate and hydroxy urethanes is obtained at the base of the splitting reactor. This procedure may be advantageous when the product removed at the base of the reactor can be used for a specific purpose or when undesirable secondary products can be removed from the splitting reactor together with the unsplit or only partly split starting material.

In general, however, the process of the present invention will be carried out in such a way that complete splitting into isocyanate and hydroxy compound is accomplished.

The products formed during the thermal splitting process, namely isocyanate and hydroxy compounds, may be removed from the splitting reactor in various ways. If both products are gaseous under the splitting conditions, they may be separated by selective condensation after leaving the splitting reactor (and after the optional separation of unreacted starting material) into a fraction A predominantly containing the isocyanate and a fraction B predominantly containing the hydroxy compound. An apparatus which has proven to be particularly suitable for the rapid and effective separation and selective condensation of the cleavage products is an apparatus made up of two fractionating columns. These columns are arranged so that the lower fractionating column is maintained at a temperature such that those constituents of the gaseous product mixture which boil at a higher temperature than the cleavage products (isocyanate and hydroxy compound), such as unreacted or only partly reacted starting material, are condensed thereon to a large extent and are thus able to flow back into the splitting reactor while the cleavage products are let through. The gas mixture escaping at the head of the first fractionating column is partially condensed on the second fractionating column in such a way that a product predominantly containing the higher boiling of the two cleavage products is formed as condensate. That part of the gas mixture passing through the second fractionating column is predominantly the lower boiling component of the two cleavage products. The condensation formed on the second fractionating column, which is either predominantly isocyanate $R^1(NCO)_x$ or predominantly hydroxy compound $R^2(OH)_y$ (depending upon the type of carbamic acid ester used) is collected in a receiver and may be distilled for further purification. The gaseous product mixture escaping at the head of the second fractionating column, which predominantly contains the lower-boiling cleavage product, may be collected in an intermediate vessel after liquefaction in a condenser kept at a suitable temperature and then redistilled.

The distillation sumps which are formed during the purification of the isocyanates $R^1(NCO)_x$ and hydroxy compounds $R^2(OH)_y$ by distillation and which consist largely of unreacted or only partly reacted starting material may be returned to the splitting reactor and subjected to the thermal splitting process again.

Carbamic acid esters which are particularly suitable for this embodiment of the present invention are those corresponding to the above-given general formulae in which the isocyanate and hydroxyl components are gaseous under the reaction conditions and which differ in their boiling points by at least 50° C. (at normal pressure) and from the boiling point of the carbamic acid ester by at least 10° C.

If the carbamic acid ester to be split and one of the cleavage products formed during the thermal splitting process differ only slightly in their respective boiling points, i.e. by 10° to 15° C. (for example with carbamic acid esters based on low-boiling monoisocyanates), it is advisable to separate the unreacted carbamic acid ester from the similarly high boiling cleavage product at a temperature near or at the boiling point of the high-boiling cleavage product with partial reflux of the high-boiling cleavage product. Such a separation process may be carried out very effectively for example in a heated column arranged between the splitting reactor and the first fractionating column. Such carbamic acid esters as well as carbamic acid esters in which one of the two cleavage products can only be distilled with difficulty (if at all) may also be split by another procedure in which the high-boiling cleavage product (i.e. the completely or substantially non-distillable cleavage product) is removed in liquid form at the base of the reactor and the cleavage product which is gaseous under the reaction conditions is removed at the head of the reactor and subsequently condensed. Where this latter procedure is adopted, it is important to select process parameters (particularly the splitting temperature) such tha the carbamic acid ester introduced will be split in the time it takes the liquid film to pass through the splitting zone. Only under such conditions can a product substantially free from unreacted starting material be removed at the base of the splitting reactor. This product (apart from any secondary constituents present) is either a monofunctional or polyfunctional isocyanate or a monofunctional or polyfunctional hydroxy compound, depending upon the type of carbamic acid ester used. If it is sufficiently pure or after it has been subjected to suitable purifying treatments, this product may be used for a wide variety of applications.

Which of the above-mentioned process variants is used for removing the cleavage products from the splitting reactor and for separating them will depend upon the type of carbamic acid ester to be split, upon the pressure prevailing in the splitting reactor and upon the splitting temperature.

Each of the above-described embodiments of the present invention may be carried out under a pressure in the range from 0.001 to 20 bars. In practice, however, it is preferred to apply a pressure in the range from 0.01 to 1.3 bars. Under pressures within this range, almost all of the hydroxy compounds and most of the isocyanates can be distilled at a temperature in the range from 150° to 450° C. Therefore, in the majority of cases the process of the present invention may be carried out by the first of the above-described embodiments in which both cleavage products are removed from the splitting reactor in gaseous form. One important exception is the thermal splitting of di- and polycarbamic acid esters of the diphenylmethane series which are formed for example in the acid-catalyzed condensation of N-phenyl carbamic acid alkyl esters with formaldehyde. Since non-distillable polyisocyanates are formed in the thermal splitting of these carbamic acid esters, only the embodiment of the the invention in which the higher boiling cleavage product is removed at the base of the reactor will be completely successful.

In cases where substantially involatile secondary products which cannot be distilled under the reaction conditions are formed in the process of the present invention, the secondary products may be removed from the splitting reactor in various ways. Where the thermal splitting process is carried out using the embodiment in which one of the two cleavage products is removed at the lower end of the splitting reactor, any substantially involatile secondary products are removed with the cleavage product flowing down the walls of the reactor. Removal of secondary products is likely to involve serious problems only where the secondary products are substantially insoluble. In the case of distillable cleavage products, the separation of the secondary products from the crude products accumulating at the base of the splitting reactor and predominantly containing the isocyanate and the hydroxy compound, may be carried out during purification of the isocyanate and the hydroxy compound by distillation. In the case of non-distillable cleavage products, purification, if necessary, may be carried out by other methods known to those in the art (for example by filtration or extraction).

The problem of removing secondary products requires particular attention when the thermal splitting process is carried out using the embodiment of the present invention in which virtually all the material introduced leaves the splitting reactor in gaseous form. Under these conditions, solid or highly viscous secondary products may accumulate in the lower part of the splitting reactor and interfere seriously with the splitting process.

One possible method for preventing or reducing accumulations of secondary products is to soften or liquefy and thereby improve the flow of the secondary products formed by increasing the temperature prevailing in the lower part of the splitting reactor. However, in many cases, an increase in temperature is not sufficient in itself. Another measure which may be appropriate is to introduce a liquid which is substantially involatile and inert under the splitting conditions (i.e. a solvent or plasticizer) into the splitting reactor at a suitable point either together with the carbamic acid ester to be split or separately through a separate metering unit. The quantity of the solvent or plasticizer used to remove substantially involatile secondary products formed depends to a large extent upon the structure of the carbamic acid ester to be split and upon the secondary constituents present therein. In general, if a solvent or plasticizer is used, it is used in a quantity of from 0.1 to 50 wt. % and preferably in a quantity of from 1 to 10 wt %, based on the quantity of carbamic acid ester used.

After removal at the base of the reactor, any secondary products present in.dissolved and/or even undissolved form in the solvent or plasticizer may be separated off, for example by filtration, distillation or extraction. The purified solvent or plasticizer may be re-used for removal of secondary products.

The following are examples of suitable solvents and plasticizers: aliphatic and cycloaliphatic hydrocarbons such as dodecane, octadecane, decalin, higher alkenes and high-boiling petroleum fractions predominantly containing alkanes; aromatic hydrocarbons such as dodecyl benzene, methyl naphthalene, benzyl naphthalene, terphenyl, diphenylmethane or biphenyl, chlorinated or ether-group-containing aromatic compounds, such as dichlorobenzene, chloronaphthalene, dichlorobenzyl naphthalene, benzyl chloronaphthalene, diphenylether, methyl naphthyl ether or pentyl naphthyl ether; sulfones, such as diphenylsulfone or naphthyl phenyl sulfone; also esters of organic and inorganic acids such as dibutyl phthalate, dioctyl phthalate, phenyl benzoate, dioctyl adipate, dioctyl sebacate, triphenyl phosphate or tricresyl phosphate.

In some case, it may also be advantageous to use compounds which would react with isocyanates under normal conditions but are present in substantially free form under the reaction conditions to remove secondary products. Compounds such as these are high-boiling alcohols and phenols such as octadecyl alcohol, benzyl alcohol, 1,6-hexane diol, tetraethylene glycol, polyethylene and polypropylene glycols, phenol, cresol, nonyl phenol or resorcinol, and other compounds commonly used as blocking agents for isocyanates.

Another possible method for removing undesirable, substantially involatile secondary products is not to evaporate the higher boiling cleavage product formed during the thermal splitting process completely but instead to allow a certain fraction thereof to run down the wall of the splitting reactor in liquid form and thereby remove any substantially involatile secondary products formed from the reaction zone. It is also possible to select reaction conditions under which a more or less large fraction of the carbamic acid ester introduced is not split or is not completely split. This ester fraction may serve as a solvent for any secondary product formed. If desired, that part of the starting material or cleavage product which is used to remove secondary products may be recovered from the product mixture accumulating at the base of the splitting reactor by a suitable separation process, for example by filtration, extraction or distillation.

In order to remove the products formed during the splitting process rapidly and effectively from the reaction zone and to prevent the cleavage products from recombining, it may be advantageous to introduce an inert gas or a compound which is liquid under normal conditions but gaseous under the reaction conditions and which is not difficult to separate from the cleavage products into the splitting reactor. Where both cleavage products are removed from the splitting reactor as gases, it may be advantageous to introduce the inert gas or the low-boiling inert liquid at a point above the splitting zone but below the fractionating columns. This alternative avoids unnecessary cooling of the reaction zone, but still effectively prevents recombination of the cleavage products in the fractionating columns.

In addition, the process of the present invention may be carried out using splitting catalysts known to those in the art. Such catalysts are described for example in German Offenlegungsschrift No. 26 35 490 and U.S. Pat. No. 3,919,279. These catalysts are used, if at all, in a quantity of from 0.001 to 5 wt % and preferably in a quantity of from 0.01 to 1 wt %, based on the weight of the carbamic acid ester used.

It is preferred to use conventional catalysts having a boiling point that is distinctly above the boiling points of the cleavage products to be removed from the splitting reactor in gaseous form, but which may be distilled off (optionally together with the solvents or plasticizers used for the removal of secondary products) and recovered for re-use. In the production of non-distillable isocyanates, it is advisable, if a catalyst is used, to use a catalyst which may readily be completely separated off by distillation from the isocyanate remaining in the distillation sump.

Compounds having a stabilizing effect may also be used as additional auxiliaries in the practical application of the process of the present invention. Examples of such stabilizing auxiliaries are acid chlorides and alkylating compounds, such as isophthalic acid dichloride or toluene sulfonic acid methyl ester. If such a stabilizing compound is used, it is generally employed in a quantity of from 0.001 to 5 wt % and preferably in a quantity of from 0.01 to 1 wt %, based on the weight of the carbamic acid ester introduced.

In view of the prior art discussed above, it must be regarded as extremely surprising that the process of the present invention makes it possible for carbamic acid esters to be thermally split to give high yields of isocyanates on which the carbamic acid esters are based. It is particularly important to note that the process of the present invention may be applied to a plurality of carbamic acid esters differing greatly in their structure. Thus, not only is it possible to split monofunctional carbamic acid esters with very short residence times, it is also possible to split carbamic acid esters of polyfunctional isocyanates and monofunctional hydroxy compounds or higher hydroxy compounds and monofunctional isocyanates effectively in the absence of solvents to form the corresponding isocyanates and hydroxy compounds. This is particularly surprising because, in conventional processes for splitting polyfunctional carbamic acid esters (see, for example, German Offenlegungsschrift No. 2,635,490, German Auslegeschriften Nos. 2,421,503 and 2,526,193 and U.S. Pat. No. 3,919,279), it is possible to obtain high yields of isocyanates only when solvents having a diluting effect are used in a large excess. Accordingly, the possibility of dispensing with the use of solvents completely or partly in the process of the present invention represents a considerable advantage over previously known processes.

The process according to the invention is illustrated by the following examples in which all the percentages quoted are percentages by weight, unless otherwise indicated.

EXAMPLES

Example 1

The apparatus used for the thermal splitting of N-methyl carbamic acid octadecyl ester was constructed as follows:

The actual splitting section was a tubular thin-layer evaporator (evaporation surface 350 cm$^2$) in which a high-speed stirrer equipped with movable metal blades extending up to the wall of the thin-layer evaporator was mounted. A heatable dropping funnel for introducing the carbamic acid ester was arranged at the head of the thin-layer evaporator. Outlets were provided at the base and head of the thin-layer evaporator for the removal of product. The lower outlet was connected through a shut-off cock to a collecting flask and the upper outlet was connected through a heat-insulated tube to a heatable Vigreux column. This column was surmounted by two coil condensers each having a tray for removing the condensates formed in the condensers arranged one behind the other. The splitting apparatus was connected to the atmosphere through a trap cooled with acetone/dry ice.

During the splitting process, molten N-methyl carbamic acid octadecyl ester was continuously introduced at a rate of 50 g/h through the dropping funnel thermostatically controlled at 100° C. into the thin-layer evaporator heated by a heat carrier oil having a temperature of 360° C. The electrically heatable Vigreux column was thermostatically controlled to a temperature of from 360° to 370° C., the lower coil condenser to a temperature of 60° C. and the upper condenser to a temperature of −20° C. The pressure prevailing in the apparatus during the splitting process amounted to 1013 mbar.

The shut-off cock at the lower outlet of the thin-layer evaporator was closed during the splitting process and was only briefly opened at intervals for removal of the substances accumulating at the base of the thin-layer evaporator during the splitting process.

During the splitting process, a stream of dried nitrogen was introduced into the apparatus at a rate of about 10 ml/minute just below the lower removal tray and was discharged into the atmosphere after passing through the fractionating columns and the trap cooled by acetone/dry ice.

The collecting flask connected to the second removal tray for the condensate predominantly containing methyl isocyanate was cooled to −20° C. The flask for collecting the condensate formed on the first condenser and the flask at the base of the thin-layer evaporator were at room temperature.

Under these conditions, the N-methyl carbamic acid octadecyl ester introduced into the thin-layer evaporator and uniformly distributed over its inner wall by the stirrer was split almost completely into methyl isocyanate and octadecanol as it flowed down the wall of the evaporator.

A product mixture which, apart from small quantities of unreacted starting material and unidentified secondary products formed during splitting, consisted predominantly of octadecanol collected at the base of the thin-layer evaporator during the splitting process. This material was periodically run off during the splitting process, but was for the most part removed on completion of the splitting process.

The gaseous product stream formed during the splitting process, which was introduced into the heated Vigreux column through the upper outlet, underwent partial condensation therein, resulting in the formation of a condensate consisting predominantly of octadecanol and N-methyl carbamic acid octadecyl ester. This condensate flowed back into the thin-layer evaporator in countercurrent to the ascending gas stream.

The gas mixture escaping at the head of the Vigreux column was separated in the two coil condensers arranged one above the other in such a way that the condensate formed on the first condenser consisted predominantly of octadecanol and the condensate formed on the second condenser consisted predominantly of methyl isocyanate.

350 g of N-methyl carbamic acid octadecyl ester were split in this way over a period of 7 hours, giving 57 g of crude methyl isocyanate (GC purity: 99%) and 277 g of crude octadecanol (GC composition: 92% by weight of octadecanol, 8% by weight of N-methyl carbamic acid octadecyl ester). In addition, 16 g of a brownish material of which 12 wt. % consisted of N-methyl carbamic acid octadecyl ester and the rest predominantly of octadecanol were removed at the base of the thin-layer evaporator.

The yield of methyl isocyanate was 92.5% of theoretical and the degree of selectivity was 99.3% of theoretical.

Example 2

The apparatus used for thermal splitting of 1-methyl-2,4-bis-(ethoxycarbonylamino)-benzene was the same as that described in Example 1 with the exception that the Vigreux column was replaced by a coil condenser which was used to separate off the cleavage products from the unreacted or only partly reacted starting material during the splitting process. This coil condenser was kept at a temperature of 165° C. by heat carrier oil.

The pressure prevailing in the apparatus was adjusted to 40 mbar and the condensers provided for the condensation of the cleavage products were cooled to 20° C. (with tap water) and to −20° C. (with cooled methanol). No carrier gas was used.

Before the beginning of the splitting process, 143.2 g of 1-methyl-2,4-bis-(ethoxy-carbonylamino)-benzene were melted, introduced into the dropping funnel at a temperature of 135° C. and then continuously introduced over a period of 3 hours into the thin-layer evaporator heated with heat carrier oil having a temperature of 300° C. At the same time, 28.0 g of tricresyl phosphate were continuously introduced through a second dropping funnel.

Under these conditions, the 1-methyl-2,4-bis-(ethoxycarbonylamino)-benzene introduced was largely split into ethanol and 2,4-tolylene diisocyanate in the splitting zone of the thin-layer evaporator. Where they escaped with the other cleavage products at the upper outlet of the thin-layer evaporator, isocyanato-urethanes formed by partial splitting of the starting material were condensed mainly on the first condenser thermostatically controlled to 165° C. and returned to the thin-layer evaporator.

The gas mixture leaving the first condenser was condensed in the two following condensers in such a way that a condensate predominantly containing a 2,4-tolylene diisocyanate and a condensate predominantly containing the ethanol were formed.

The following data were determined on completion of the splitting process:

41.1 g of condensate predominantly containing ethanol were obtained; 94.4 wt % of this condensate consisted of ethanol and 5.5 wt % was 1-methyl-2,4-bis-(ethoxycarbonylamino)-benzene. The condensate predominantly containing the isocyanate was obtained in a quantity of 100.5 g. 52.7 wt. % of this condensate was 2,4-tolylene diisocyanate, 0.9 wt. % was 1-methyl-2,4-bis-(ethoxycarbonylamino)-benzene, 44.4 wt. % was 1-methyl-2-(ethoxycarbonylamino)-4-isocyanatobenzene and 1-methyl-2-isocyanato-4-(ethoxycarbonylamino)-benzene and 2.0 wt. % was tricresyl phosphate.

A total of 27.5 g of a cloudy, brownish liquid was collected at the base of the thin-layer evaporator. 85 wt % of this liquid could be distilled in a vacuum of 1 mbar.

The yield of 2,4-tolylene diisocyanate was 56.5% of theoretical and the selectivity was 96.4% of theoretical. The yield of ethanol was 78.3% of theoretical and the selectivity was 99.4% of theoretical.

Example 3

Thermal splitting of a mixture of 80% of 1-methyl-2,4-bis-(ethoxycarbonylamino)-benzene and 20% of 1-methyl-2,6-bis-(ethoxycarbonylamino)-benzene in the presence of a catalyst was carried out in the splitting apparatus described in Example 2. The thin-layer evaporator installed had an increased evaporation surface of 900 cm$^2$.

The thermal splitting process was carried out under a pressure of 10 mbar. The thin-layer evaporator was heated by a heat carrier oil having a temperature of 240° C. The coil condensers of the fractionating columns were thermostatically controlled to 135° C., 20° C. and −25° C., respectively.

During the 3-hours-long splitting process, a homogeneous mixture of 645 g of the above-mentioned carbamic acid ester, 32 g of phenyl-(1,2,3,4-tetrahydro-5(6)-naphthyl)-sulfone and 2.0 g of dibutyl tin dilaurate was continuously introduced into the thin-layer evaporator from the dropping funnel heated to 135° C.

The gaseous product stream was split (as described in Example 2) into a fraction consisting predominantly of 2,4-tolylene diisocyanate and 2,6-tolylene diisocyanate and a fraction consisting predominantly of ethanol. The non-gaseous product fractions were removed together with the solvent used at the base of the thin-layer evaporator.

The condensate obtained on completion of the splitting process, which consisted predominantly of ethanol, amounted to 243.2 g of which 63.4 wt. % was ethanol and 36.6 wt. % was 1-methyl-2,4-(2,6)-bis-(ethoxycarbonylamino)-benzene. The isocyanate-containing condensate was obtained in a quantity of 395.7 g of which 56.4 wt. % was (2,4)- and (2,6)-tolylene diisocyanate, 39.1 wt. % was 1-methyl-2(4)-(ethoxycarbonylamino)-4(2)-isocyanatobenzene and 1-methyl-2-(ethoxycarbonylamino)-6-isocyanatobenzene, 3.1 wt. % was 1-methyl-2,4(2,6)-bis-(ethoxycarbonylamino)-benzene and 5.5 wt. % was phenyl-(1,2,3,4-tetrahydro-5(6)-naphthyl)-sulfone.

The quantity of the cloudy, brownish product obtained at the base of the thin-layer evaporator amounted to 38 g.

From the above-mentioned data, the yield of 2,4(2,6)-tolylene diisocyanate was calculated to be 52.9% of theoretical (selectivity of 97.6% of theoretical) and the yield of ethanol to be 69.1% of theoretical (selectivity of 99.2% of theoretical).

Example 4

The apparatus used for thermal splitting of 1-(ethoxycarbonylamino-3,3,5-trimethyl-5-(ethoxycarbonylamino-methyl)-cyclohexane was the same as that described in example 2 the thinlayer evaporator is heated by a heat carrier oil having a temperature of 290° C. The coil condenser is kept at a temperature of 170° C., the pressure in the apparatus is kept at 12 mbar.

A homogeneous mixture heated to 120° C. and consisting of 400 g of 1-(ethoxycarbonylamino)-3,3,5-trimethyl-5-(ethoxycarbonylamino-methyl)-cyclohexane, 30 g of dichlorobenzyl naphthalene and 3 g of dibutyl-tin-dilaurate is introduced continuously into the apparatus within 5 hours.

The gaseous products which formed during the thermal splitting process are separated as described in example 2 into two fractions consisting predominantly of 1-isocyanato-3,3,5-trimethyl-5-isocyanato-methyl-cyclohexane resp. of ethanol. The non-gaseous products and the plasticiser are removed at the bottom of the thin-layer evaporator.

Following products were obtained: 115.4 g of an ethanol fraction (77.1 % of ethanol, 22.6 % of 1-(ethoxycarbonylamino)-3,3,5-trimethyl-5-ethoxycarbonylamino-methyl)-cyclohexane and 0.3 % of dichlorobenzyl naphthalene), 264 g of a diisocyanate fraction (55.5 % of 1-isocyanato-3,3,5-(isocyanatomethyl)-cyclohexane, 43.2 % of 1-(ethoxycarbonylamino)-3,3,5-trimethyl-5-(isocyanatomethyl)-cyclohexane resp. 1-isocyanato-3,3,5-trimethyl-5-(ethoxycarbonylamino-methyl)-cyclohexane, 1.3 % of dichlorobenzyl naphthalene. 39.8 g of non-volatile residue is removed from the bottom of the thin-layer evaporator.

The yield of diisocyanate corresponds to 51.8 % of the theoretical yield (selectivity: 91.9% ) the yield of ethanol corresponds to 75.8% of the theoretical yield (selectivity: 98.9%).

Example 5

The apparatus used for thermal splitting of N-butylcarbamic acid octadecyl ester corresponds to the apparatus described in example 2. The coil condenser was kept at a temperature of 140°C. The isocyanate passing through the coil condenser was condensed in a further condenser cooled to −15° C.

Within 6 hours 240 g of N-butylcarbamic acid octadecyl ester heated to 120° C. are continuously introduced into the thin film evaporator heated with heat carrier oil having a temperature of 380° C. Under these conditions the starting material is uniformly distributed over the inner walls of the thin layer evaporator by the stirrer and split as it flowed down the wall of the evaporator. Simultaneously dry nitrogen was introduced into the apparatus at a rate of 300 ml/h.

56 g of butylisocyanate having a purity of 94.8% are obtained as overhead product whereas 182 g of a mixture of 84 mol % of octadecanol and 16 mol-% of N-butylcarbamic acid octadecyl ester are obtained as bottom product. The yield of butylisocyanate corresponds to 82.5 % of the theoretical (selectivity: 98.1 %).

Example 6

The apparatus used for splitting 2,2-bis-(4-N-butylcarbamoyloxycyclohexyl)-propane was the the same as described in example 2. The coil condenser was kept at a temperature of 120° C.

300 g of 2,2-bis-(4-N-butylcarbamoyloxy-cyclohexyl)-propane heated to 160° C. are continously introduced within 4,5 hours into the thin film evaporator which was heated to 370° C. Simultaneously dry nitrogen is introduced into the apparatus at a rate 65 ml/h.

78 g of butylisocyanate (purity: 96.4 %) are obtained as overhead product which was condensed at -20° C. as described in example 5. At the bottom of the apparatus 209 g of an alcohol fraction consisting of 21 % of 2,2-bis-(4-hydroxycyclohexyl)-propane and 79 % of 2-(4-N-butylcarbamoyloxy-cyclohexyl)-2-(4-hydroxycyclohexyl)-propane are obtained. This corresponds to a yield of butylisocyanate of 55.5 % of the theoretical yield (selectivity: 92.8 %).

What is claimed is:

1. A continuous process for thermally splitting N-monosubstituted carbamic acid esters comprising:
   (a) thermally splitting an N-monsubstituted carbamic acid ester which is flowed down or passed over an inner wall of a tube reactor at a temperature of from 150° to 450° C. and under a pressure of from 0.001 to 20 bar into a fraction which is predominantly isocyanate and a fraction which is predominantly hydroxyl compound; and
   (b) removing any gaseous fraction formed under the splitting conditions at the head of the tube reactor and collecting any liquid fraction which accumulates at the base of the tube reactor under the splitting conditions.

2. The process of claim 1 in which the tube reactor is a tubular thin-layer or falling-film evaporator.

3. The process of claim 1 in which the isocyanate and the hydroxyl fractions are removed together in gaseous form at the head of the tubular reactor and subsequently separated by selective condensation.

4. The process of claim 1 in which the isocyanate fraction is removed in gaseous form at the head of the reactor and the hydroxyl fraction is removed in liquid form at the base of the reactor.

5. The process of claim 1 in which the hydroxyl fraction is removed in gaseous form at the head of the reactor and the isocyanate fraction is removed in liquid form at the base of the reactor.

6. The process of claim 1 in which the thermal splitting is conducted in the presence of a catalyst which accelerates the splitting reaction.

7. The process of claim 6 in which the thermal splitting is conducted in the presence of a compound which stabilizes the isocyanate and hydroxyl fractions.

8. The process of claim 1 in which the thermal splitting is conducted in the presence of a compound which stabilizes the isocyanate and hydroxyl fractions.

9. The process of claim 1 in which the thermal splitting is conducted in the presence of small quantities of high boiling liquids that are inert under the splitting conditions.

10. The process of claim 1 in which the N-mono-substituted carbamic acid ester corresponds to the following:

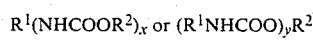

in which

R¹ represents an aliphatic hydrocarbon radical having from 1 to 18 carbon atoms optionally containing an inert substituent and/or being olefinically unsaturated, a cycloaliphatic hydrocarbon radical having from 3 to 18 carbon atoms optionally containing an inert substituent and/or being olefinically unsaturated, an araliphatic hydrocarbon radical having from 7 to 18 carbon atoms and optionally containing an inert substituent, or an aromatic hydrocarbon radical having from 6 to 18 carbon atoms and optionally containing an inert substituent, R² represents an aliphatic hydrocarbon radical having from 1 to 18 carbon atoms optionally containing an inert substituent and/or being olefinically unsaturated, a cycloaliphatic hydrocarbon radical having from 4 to 18 carbon atoms and optionally containing an inert substituent and/or being olefinically unsaturated, an araliphatic hydrocarbon radical having 7 to 18 carbon atoms and optionally containing an inert substituent, or an aromatic hydrocarbon radical having from 6 to 12 carbon atoms and optionally containing an inert substituent, and x and y each represent a number from 1 to 3 and has a boiling point which is at least 10° C. higher than that of the higher boiling of the isocyanate and hydroxyl fractions with the isocyanate and hydroxyl fractions having boiling points which differ from each other by at least 50° C. at normal pressure.

* * * * *